United States Patent [19]

Shoshi et al.

[11] Patent Number: 5,314,997

[45] Date of Patent: May 24, 1994

[54] OPTICALLY ACTIVE AZO COMPOUND, PRODUCING METHOD THEREOF, AND LIQUID CRYSTAL COMPOSITION CONTAINING SAID COMPOUND

[75] Inventors: Masayuki Shoshi; Akihiko Kanemoto, both of Yokohama, Japan

[73] Assignee: Ricoh Company, Ltd., Tokyo, Japan

[21] Appl. No.: 904,555

[22] Filed: Jun. 26, 1992

[30] Foreign Application Priority Data

Jul. 11, 1991 [JP] Japan .................................. 3-171227

[51] Int. Cl.$^5$ ..................... C07C 245/08; C09K 19/24
[52] U.S. Cl. .................................. 534/577; 534/843; 252/299.68
[58] Field of Search ............................. 534/577, 843; 252/299.68

[56] References Cited

U.S. PATENT DOCUMENTS

| | | | |
|---|---|---|---|
| 3,815,972 | 6/1974 | Hsieh .............................. | 534/577 X |
| 3,893,994 | 7/1975 | Steinstrasser .................... | 534/577 |
| 3,984,392 | 10/1976 | Van der Veen et al. ......... | 534/577 |
| 4,138,358 | 2/1979 | Labes ............................. | 534/299.68 |
| 4,633,012 | 12/1986 | Taguchi et al. ............. | 252/299.68 X |
| 4,634,842 | 2/1987 | Taguchi et al. ............. | 252/299.68 X |
| 4,874,545 | 10/1989 | Heppke et al. .............. | 252/299.68 X |
| 4,921,728 | 5/1990 | Takiguchi et al. .................... | 427/58 |
| 4,979,805 | 12/1990 | Yoshinaga et al. ............. | 534/577 X |
| 5,076,962 | 12/1991 | Furukawa et al. ............. | 252/299.68 |

*Primary Examiner*—Mary C. Lee
*Assistant Examiner*—Fiona T. Powers
*Attorney, Agent, or Firm*—Oblon, Spivak, McClelland, Maier & Neustadt

[57] ABSTRACT

An optically active azo compound is represented by the following general formula (I),

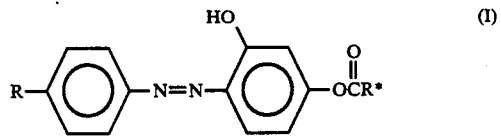

where R is an alkyl group having from 1 to 20 carbon atoms, and R* is an optically active radical of an alkyl group or a halogen substituted alkyl group having from 1 to 10 carbon atoms. A liquid crystal composition contains this compound. A method for producing an optically active azo compound represented by the following general formula (I) has the step of reacting a phenol compound represented by the following general formula (II) with an optically active carboxylic acid represented by the following general formula (III) using a condensing agent at a room temperature.

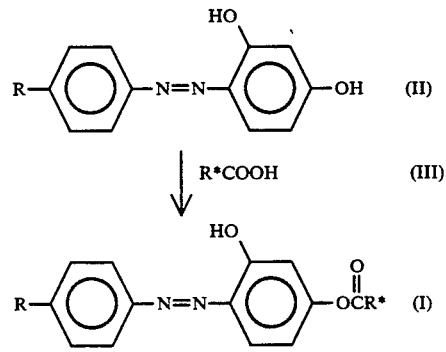

3 Claims, 2 Drawing Sheets

OPTICALLY ACTIVE AZO COMPOUND, PRODUCING METHOD THEREOF, AND LIQUID CRYSTAL COMPOSITION CONTAINING SAID COMPOUND

BACKGROUND OF THE INVENTION

1. Field of the Invention

The present invention relates to a novel optically active azo compound, a producing method thereof, and a liquid crystal composition containing said compound.

2. Description of the Related Art

Each of liquid crystal materials is widely used as an element for a display at the present time. These liquid crystal display elements are almost constructed by a display system of a twisted nematic type (TN-type) using a nematic liquid crystal. This display system has many merits and advantages. However, responsibility of the display system is very low in comparison with that of a display system of a light emitting type such as a CRT. No responsibility can be easily improved although many liquid crystal display systems except for the display system of the TN-type are also considered.

However, a liquid crystal device using a ferroelectric smectic liquid crystal has a high response speed 100 to 1000 times that of the general liquid crystal display element of the TN-type. Further, this liquid crystal device has preferable bistability. Accordingly, displayed contents are memorized even when a power source of the liquid crystal device is turned off. Such a memory effect has been recently found. Therefore, there is a high possibility that such a liquid crystal device can be used for an optical shutter, a printer head, a thin type television, etc. The liquid crystal device is searched and developed at the present time to practically use this device in various kinds of industrial fields.

A phase of the ferroelectric liquid crystal belongs to a chiral smectic phase of a tilting system. A practically desirable liquid crystal phase of the ferroelectric liquid crystal is a so-called chiral smectic C-phase having low viscosity.

For example, the following properties are required with respect to such a ferroelectric liquid crystal material.

(1) The ferroelectric liquid crystal material is chemically stable and has excellent durability.

(2) The ferroelectric liquid crystal material has a wide liquid crystal phase in a temperature range from a low temperature to a high temperature and shows ferroelectricity in a wide temperature range including a room temperature.

(3) The rotational viscosity of a liquid crystal molecule in the ferroelectric liquid crystal material is small and the ferroelectric liquid crystal material has large spontaneous polarization and high speed responsibility.

For example, various kinds of liquid crystal compounds are already synthesized on the basis of such material designs in Japanese Patent Application Laying Open (KOKAI) Nos. Hei 2-225441 and Hei 2-229131, etc. However, at the present stage, it is difficult to obtain a practical material constituting a ferroelectric liquid crystal constructed by a single composition and satisfying the above-mentioned various properties. Similar to the case of a nematic liquid crystal already used practically, there is a trial for obtaining desirable characteristics for the ferroelectric liquid crystal by mixing several kinds of compounds with each other.

SUMMARY OF THE INVENTION

It is therefore a first object of the present invention to provide a novel optically active azo compound and a liquid crystal composition containing said compound, which are chemically stable and have a high response speed and can be used in a guest-host mode in the case of a liquid crystal material suitable for an optical switching system, especially, a composition constructed by mixing several kinds of compounds with each other.

A second object of the present invention is to provide a method for producing the optically active azo compound.

The above first object of the present invention can be achieved by an optically active azo compound represented by the following general formula (I),

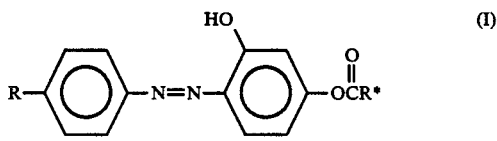

where R is an alkyl group having from 1 to 20 carbon atoms, and R* is an optically active group of an alkyl group or a halogen substituted alkyl group, having from 1 to 10 carbon atoms.

The above second object of the present invention can be achieved by a method for producing an optically active azo compound represented by the following general formula (I), wherein a phenol compound represented by the following general formula (II) react with an optically active carboxylic acid represented by the following general formula (III) using a condensing agent at a room temperature.

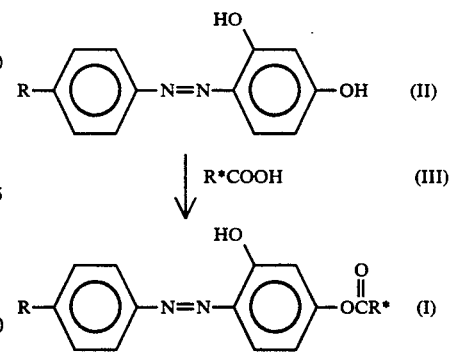

In accordance with the above structures of the present invention, the optically active azo compound and the liquid crystal composition containing said compound are chemically stable and have a high response speed and can be used in a guest-host mode in the case of a liquid crystal material suitable for an optical switching system, especially, a composition constructed by mixing several kinds of compounds with each other.

Further objects and advantages of the present invention will be apparent from the following description of the preferred embodiments of the present invention as illustrated in the accompanying drawings.

DESCRIPTION OF THE PREFERRED EMBODIMENTS

Figure 1:
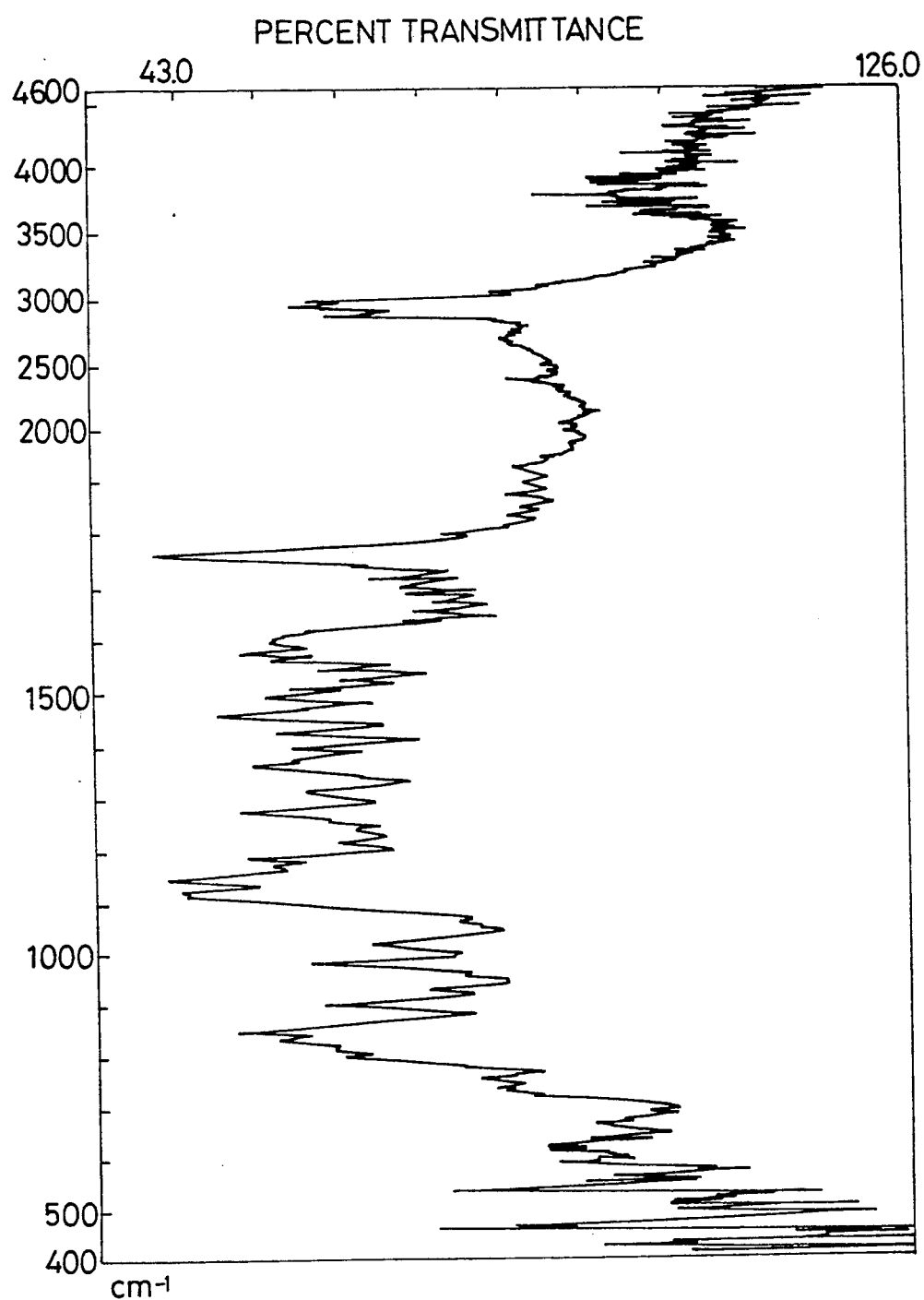
FIG. 1 is a graph showing an infrared absorption spectrum of an optically active azo compound (compound No. 1) obtained in Embodiment 1 of the present invention.

The preferred embodiments of an optically active azo compound, a producing method thereof, and a liquid crystal composition including this compound in the present invention will next be described in detail.

In the present invention, an optically active azo compound as one specified compound group has a chemical structure represented by the following general formula (I).

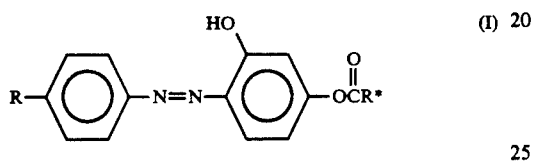
(I)

In this formula (I), R is an alkyl group having from 1 to 20 carbon atoms. R* is an optically active radical of an alkyl group or a halogen substituted alkyl group, having from 1 to 10 carbon atoms. Further, a liquid crystal composition in the present invention contains the optically active azo compound represented by the above general formula (I).

Largest features of the optically active azo compound represented by the above general formula (I) are characterized in that a liquid crystal skeleton has an azo dye skeleton. Accordingly, a response speed can be greatly increased in comparison with that in a guest-host mode of the general compound containing a dye. Further, the response speed can be also increased in birefringence in addition to the case of the guest-host mode since viscosity of the optically active azo compound is low.

The compounds including in the optically active azo compound represented by the above general formula (I) are shown concretely in the following Tables 1 to 3.

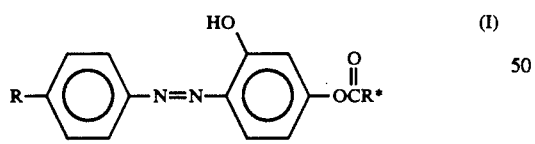
(I)

TABLE 1

| compound No. | R | R* |
|---|---|---|
| (1) | $C_6H_{13}-$ | $-\overset{*}{C}HC_2H_5$ with $CH_3$ |
| (2) | $C_6H_{13}-$ | $-\overset{*}{C}H-\overset{*}{C}HC_2H_5$ with Cl, $CH_3$ |
| (3) | $C_6H_{13}-$ | $-\overset{*}{C}HCH_2CH(CH_3)_2$ with Cl |

TABLE 1-continued

| compound No. | R | R* |
|---|---|---|
| (4) | $C_6H_{13}-$ | $-\overset{*}{C}HCH(CH_3)_2$ with Cl |
| (5) | $C_7H_{15}-$ | $-\overset{*}{C}HC_2H_5$ with $CH_3$ |
| (6) | $C_7H_{15}-$ | $-\overset{*}{C}H-\overset{*}{C}HC_2H_5$ with Cl, $CH_3$ |
| (7) | $C_7H_{15}-$ | $-\overset{*}{C}HCH_2CH(CH_3)_2$ with Cl |
| (8) | $C_7H_{15}-$ | $-\overset{*}{C}HCH(CH_3)_2$ with Cl |
| (9) | $C_8H_{17}-$ | $-\overset{*}{C}HC_2H_5$ with $CH_3$ |
| (10) | $C_8H_{17}-$ | $-\overset{*}{C}H-\overset{*}{C}HC_2H_5$ with Cl, $CH_3$ |
| (11) | $C_8H_{17}-$ | $-\overset{*}{C}HCH_2CH(CH_3)_2$ with Cl |

TABLE 2

| compound No. | R | R* |
|---|---|---|
| (12) | $C_8H_{17}-$ | $-\overset{*}{C}HCH(CH_3)_2$ with Cl |
| (13) | $C_9H_{19}-$ | $-\overset{*}{C}HC_2H_5$ with $CH_3$ |
| (14) | $C_9H_{19}-$ | $-\overset{*}{C}H-\overset{*}{C}HC_2H_5$ with Cl, $CH_3$ |
| (15) | $C_9H_{19}-$ | $-\overset{*}{C}HCH_2CH(CH_3)_2$ with Cl |
| (16) | $C_9H_{19}-$ | $-\overset{*}{C}HCH(CH_3)_2$ with Cl |
| (17) | $C_{10}H_{21}-$ | $-\overset{*}{C}HC_2H_5$ with $CH_3$ |
| (18) | $C_{10}H_{21}-$ | $-\overset{*}{C}H-\overset{*}{C}HC_2H_5$ with Cl, $CH_3$ |
| (19) | $C_{10}H_{21}-$ | $-\overset{*}{C}HCH_2CH(CH_3)_2$ with Cl |

TABLE 2-continued

| compound No. | R | R* |
|---|---|---|
| (20) | $C_{10}H_{21}-$ | $-\overset{*}{C}H CH(CH_3)_2$ with Cl |
| (21) | $C_{12}H_{26}-$ | $-\overset{*}{C}H C_2H_5$ with $CH_3$ |
| (22) | $C_{12}H_{25}-$ | $-\overset{*}{C}H-\overset{*}{C}H C_2H_5$ with Cl, $CH_3$ |

TABLE 3

| compound No. | R | R* |
|---|---|---|
| (23) | $C_{12}H_{25}-$ | $-\overset{*}{C}H CH_2CH(CH_3)_2$ with Cl |
| (24) | $C_{12}H_{25}-$ | $-\overset{*}{C}H CH(CH_3)_2$ with Cl |
| (25) | $C_{14}H_{29}-$ | $-\overset{*}{C}H C_2H_5$ with $CH_3$ |
| (26) | $C_{14}H_{29}-$ | $-\overset{*}{C}H-\overset{*}{C}H C_2H_5$ with Cl, $CH_3$ |
| (27) | $C_{14}H_{29}-$ | $-\overset{*}{C}H CH_2CH(CH_3)_2$ with Cl |
| (28) | $C_{14}H_{29}-$ | $-\overset{*}{C}H CH(CH_3)_2$ with Cl |

In the above Table 1 to 3, mark * designates optically active carbon.

The compound represented by the general formula (I) and provided in each of the above concrete compounds can be obtained by reacting a phenolic compound represented by the following general formula (II) with an optically active carboxylic acid compound represented by the following general formula (III) using a condensing agent at a room temperature.

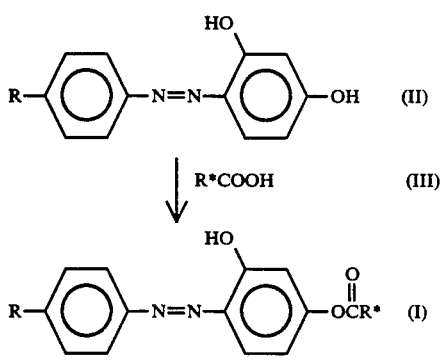

A compound, such as N',N'dicyclohexylcarbodiimide and N, N'-carbonyldiimidazole are used as the condensing agent. Tetrahydrofuran, methylene chloride, 1, 2-dichloroethane, acetonitrile, etc. are used as a solvent. The compound represented by the general formulas (II) and (III) may be provided at a stoichiometric ratio.

For example, the compound represented by the general formula (II) can be obtained in accordance with the following reaction formula.

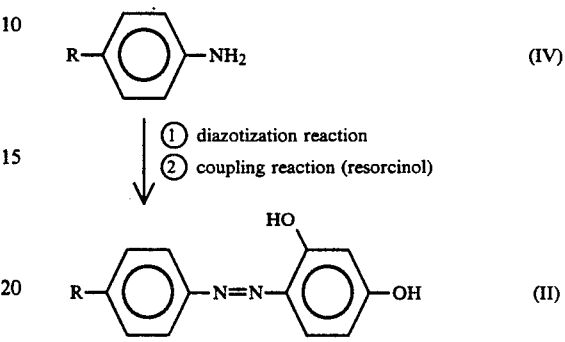

Namely, aniline derivatives represented by the general formula (IV) are first diazotized in accordance with a normal method and next proceeded coupling-reaction with resorcinol, so that the compound represented by the general formula (II) can be easily obtained.

The optically active carboxylic acid compound represented by the general formula (III) can be obtained by using a compound sold at a market. Otherwise, said compound can be synthesized from an optically active aminoacid by a well-known method as shown in Bull. Soc. Chem. Bio. 28, 497(1946), and others.

The optically active azo compound represented by the general formula (I) in the present invention has an excellent property as a ferroelectric liquid crystal material, especially, as a liquid crystal composition. That is, said compound has a high speed of response and is chemically stable.

The novel optically active azo compound represented by the general formula (I) in the present invention can not be used as a ferroelectric liquid crystal in itself. This optically active azo compound is mixed with a smectic liquid crystal which is not chiral, in itself or is mixed with another ferroelectric liquid crystal to form a composition, thereby showing an excellent property.

It is effective to prevent a reverse domain from being generated in a TN-type cell by adding the optically active azo compound represented by the general formula (I) to a nematic liquid crystal. In this case, it is preferable to use the optically active azo compound such that a mixture ratio of the optically active azo compound represented by the general formula (I) is equal to 0.01 to 50%, based on the weight of the liquid crystal composition.

The optically active azo compound can be added to a smectic liquid crystal or a chiral smectic liquid crystal, so that this compound can be used as a chiral smectic liquid crystal. The optically active azo compound can be used as a liquid crystal composition in a guest-host type liquid crystal element such as a liquid crystal element of a phase transition type. In this case, it is preferable to use the optically active azo compound such that a mixture ratio of the optically active azo compound represented by the general formula (I) is equal to 0.01 to 80%, based on the weight of the liquid crystal composition.

Further, the optically active azo compound in the present invention can be suitably used not only for a display, but also for various kinds of electronic optical devices in a field of optoelectronics such as an electronic optical shutter, an electronic optical diaphragm, an optical modulator, a switch for switching optical communication paths, a memory, a varifocal lens, and others.

The present invention will next be described further in detail on the basis of the following Exercises, but is not limited to these Exercises. In the concrete Exercises, the values of a melting point and a phase transition temperature are slightly changed in accordance with a measuring method and the purity of each compound.

EXAMPLE 1

Production of optically active 4-hexyl-2'-hydroxy-4'-(2-methylbutanoyloxy)azobenzene (compound No. 1)

A. Production of 4-hexyl-2',4'-dihydroxyazobenzene

6N-HCl of 89 ml and water of 89 ml are added to 4-hexylaniline of 25 g and are heated and stirred for one hour at the temperature of 800° C. Thereafter, sodium nitrite of 10.12 g is dissolved in water of 25 ml at a cooling temperature from 0° to −50° C. This dissolved solution is dropped for twenty minutes and is then stirred continuously for two hours at this cooling temperature. This stirred solution is added to a solution obtained by dissolving resorcinol of 29.36 g in water of 1 liter in a temperature range from 0° to 50° C. Further, sodium acetate for neutralization is gradually added to the added solution in this temperature range. Thereafter, This neutralized solution is continuously stirred for about one hour and an obtained crystal is filtered. This crystal is sufficiently washed in water and is dried in a desiccator. Silica gel column chromatography processing using 1, 2 dichloroethane as a developing solvent is then performed with respect to this crystal. Thus, a crude aimed substance is obtained and is further recrystallized by toluene, so that an aimed substance of 17.85 g is finally obtained. A decomposition point of this aimed substance and the results of an elementary analysis thereof are provided as follows.

Decomposition point: 1240° C.
Elementary analysis

|       | measured values | calculated values |
|-------|-----------------|-------------------|
| C (%) | 72.53           | 72.46             |
| H (%) | 7.58            | 7.43              |
| N (%) | 9.21            | 9.39              |

B. Production of optically active 4-hexyl-2'-hydroxy-4'-(2-methylbutanoyloxy)azobenzene (compound No. 1)

4-hexyl-2',4'-dihydroxyazobenzene of 2.98 g (0.01 mol) obtained in the above item A, optically active 2-methylbutyric acid of 1.02 g (0.01 mol), N, N'-dicyclohexylcarbodiimide of 2.06 g (0.01 mol), and 4-dimethylaminopyridine of 0.12 g (0.001 mol) are stirred in methylene chloride of 150 ml for about five hours at a room temperature and is left as it is for one night. A crystal is then filtered and silica gel column chromatography processing using toluene as a developing solvent is performed with respect to a residue obtained by distilling the methylene chloride from the filtered crystal. An obtained coarse object substance is recrystallized three times by ethanol so that a pure object substance (compound No. 1) of 1.20 g is finally obtained.

The structure of this compound No. I is confirmed by an infrared absorption spectrum shown in FIG. 1.

EXAMPLE 2 TO 4

Compound No. 2 of 1.40 g, compound No. 3 of 0.82 g and compound No. 4 of 2.0 g as a pure aimed substance are obtained in the same method as the item B in the Example 1 except that optically active 2-chloro-3-methylvaleric acid of 1.51 g, optically active 2-chloro-4-methylvaleric acid of 1.51 g, and optically active 2-chloro-3-methylbutyric acid of 1.37 g are used instead of optically active 2-methylbutyric acid.

EXAMPLE 5

Production of optically active 4-heptyl-2'-hydroxy-4'-(2-methylbutanoyloxy)azobenzene (compound No. 5)

C. Production of 4-heptyl-2',4'-dihydroxyazobenzene

A pure aimed substance of 29.07 g is obtained in the same method as the item A in the Example 1 except that 4-heptylaniline of 27 g is used instead of 4-hexylaniline. A decomposition point of this aimed substance and the results of an elementary analysis thereof are provided as follows.

Decomposition point: 128.50° C.
Elementary analysis

|       | measured values | calculated values |
|-------|-----------------|-------------------|
| C (%) | 73.15           | 73.04             |
| H (%) | 7.90            | 7.74              |
| N (%) | 8.75            | 8.97              |

D. Production of optically active 4-heptyl-2'-hydroxy-4'-(2-methylbutanoyloxy)azobenzene (compound No. 5)

A pure aimed substance (compound No. 5) of 1.01 g is obtained in the same method as the item B in the Example 1 except that 4-heptyl-2',4'-dihydroxyazobenzene of 3.12 g obtained in the above item C is used instead of 4-hexyl-2',4'-dihydroxyazobenzene.

EXAMPLE 6 TO 8

Compound No. 6 of 1.53 g, compound No. 7 of 1.03 g and compound No. 8 of 1.82 g as a pure aimed substance are obtained in the same method as the item D in the Example 5 except that optically active 2-chloro-3-methylvaleric acid of 1.51 g, optically active 2-chloro-4-methylvaleric acid of 1.51 g, and optically active 2-chloro-3-methylbutyric acid of 1.37 g are used instead of optically active 2-methylbutyric acid.

EXAMPLE 9

Production of optically active 4-octyl-2'-hydroxy-4'-(2-methylbutanoyloxy)azobenzene (compound No. 9)

E. Production of 4-octyl-2',4'-dihydroxyazobenzene

A pure aimed substance of 16.33 g is obtained in the same method as the item A in the Production 1 except that 4-octylaniline of 28.95 g is used instead of 4-hexylaniline. A decomposition point of this aimed substance and the results of an elementary analysis thereof are provided as follows.

Decomposition point: 128.50° C.
Elementary analysis

|   | measured values | calculated values |
|---|---|---|
| C (%) | 66.72 | 66.56 |
| H (%) | 7.11 | 6.98 |
| N (%) | 7.65 | 7.76 |

F. Production of 4-octyl-2'-hydroxy-4'-(2'-methylbutanoyloxy)azobenzene (compound No. 9)

A pure aimed substance (compound No. 9) of 1.29 g is obtained in the same method as the item B in the Example 1 except that 4-octyloxyazobenzene of 3.26 g obtained in the above item E is used instead of 4-hexyl-2',4'-dihydroxyazobenzene.

EXAMPLE 10 TO 12

Compound No. 10 of 0.91 g, compound No. 11 of 0.53 g and compound No. 12 of 0.60 g as a pure aimed substance are obtained in the same method as the item F in the Example 9 except that optically active 2-chloro-3-methylvaleric acid of 1.51 g, optically active 2-chloro-4-methylvaleric acid of 1.51 g, and optically active 2-chloro-3-methylbutyric acid of 1.37 g are used instead of optically active 2-methylbutyric acid.

Figure 2:
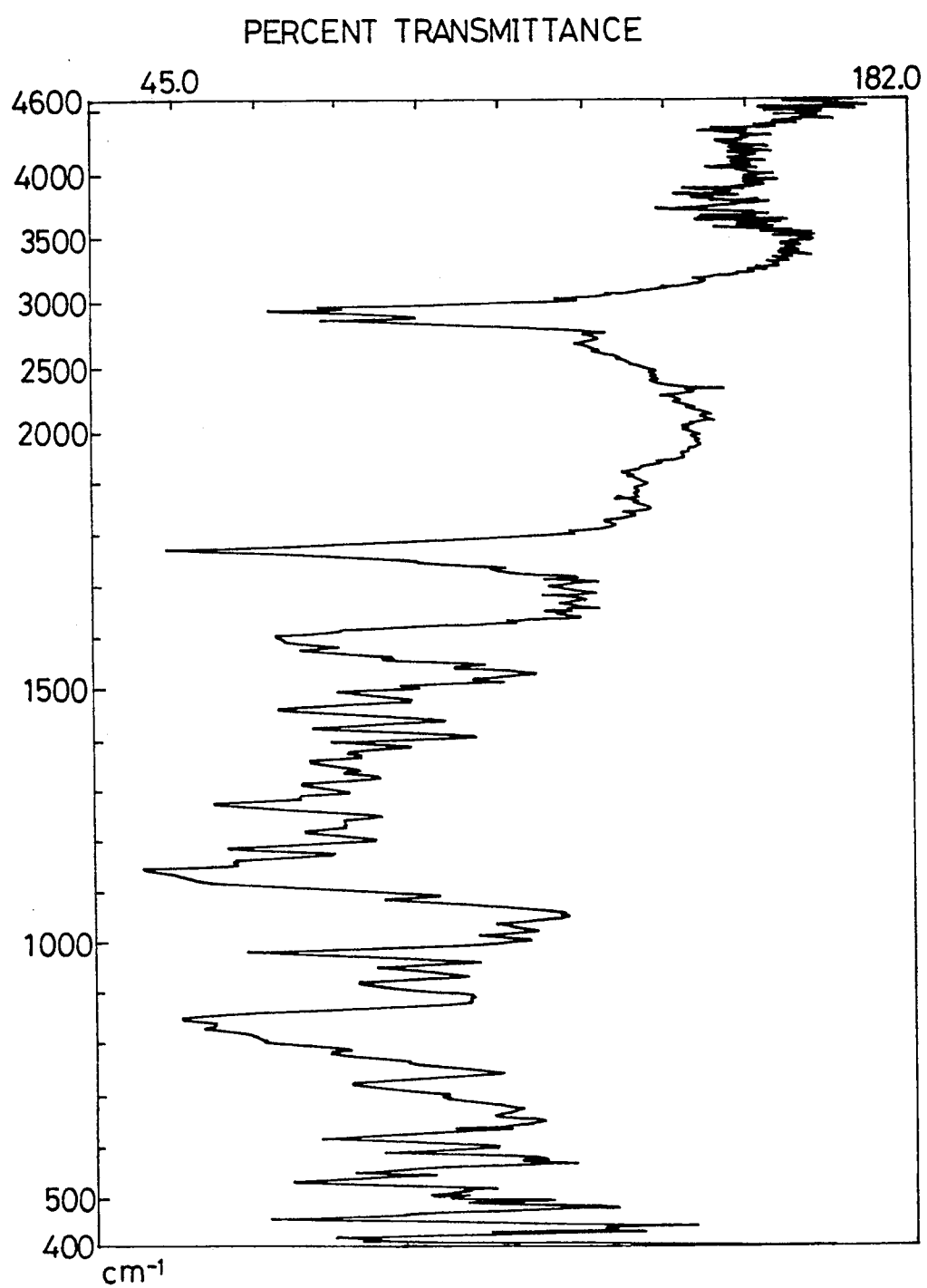
FIG. 2 is a graph showing an infrared absorption spectrum of an optically active azo compound (compound No. 10) obtained in Embodiment 10 of the present invention.

The structure of this compound No. 10 is confirmed by an infrared absorption spectrum shown in FIG. 2.

EXAMPLE 13

Production of optically active 4-decyl-2'-hydroxy-4'-(2-methylbutanoyloxy)azobenzene (compound No. 17)

G. Production of 4-decyl-2',4'-dihydroxyazobenzene

A pure aimed substance of 15.48 g is obtained in the same method as the item A in the Example 1 except that 4-decylaniline of 32.91 g is used instead of 4-hexylaniline. A decomposition point of this aimed substance and the results of an elementary analysis thereof are provided as follows.

Decomposition point: 129.50° C.
Elementary analysis

|   | measured values | calculated values |
|---|---|---|
| C (%) | 74.62 | 74.54 |
| H (%) | 8.61 | 8.53 |
| N (%) | 7.80 | 7.90 |

H. Production of optically active 4-decyl-2'-hydroxy-4'-(2-methylbutanoyloxy)azobenzene (compound No. 17)

A pure aimed substance (compound No. 17) of 1.23 g is obtained in the same method as the item B in the Example 1 except that 4-decyl-2',4'-dihydroxyazobenzene of 3.54 g obtained in the above item G is used instead of 4-hexyl-2',4'-dihydroxyazobenzene.

EXAMPLE 14 TO 16

Compound No. 18 of 1.86 g, compound No. 19 of 0.81 g and compound No. 20 of 1.30 g as a pure aimed substance are obtained in the same method as the item H in the Example 13 except that optically active 2-chloro-3-methylvaleric acid of 1.51 g, optically active 2-chloro-4-methylvaleric acid of 1.51 g, and optically active 2-chloro-3-methylbutyric acid of 1.37 g are used instead of optically active 2-methylbutyric acid.

Melting points (phase transition temperatures) of the above obtained compounds and the results of an elementary analysis thereof are shown in the following Table 4.

TABLE 4

| Example No. | compound No. | melting point (phase transition temperature) °C. C N I | elementary analysis | measured values (%) | calculated values (%) |
|---|---|---|---|---|---|
| 1 | 1 | 68.3 |  | C 72.30 | 72.22 |
|   |   |   |  | H 7.98 | 7.91 |
|   |   | 57.1 |  | N 7.11 | 7.32 |
| 2 | 2 | 67.2 |  | C 66.84 | 66.89 |
|   |   |   |  | H 7.47 | 7.25 |
|   |   | 56.0 |  | N 6.44 | 6.50 |
| 3 | 3 | 60.0 |  | C 66.86 | 66.89 |
|   |   |   |  | H 7.37 | 7.25 |
|   |   | 42.6 (44.1) |  | N 6.40 | 6.50 |
| 4 | 4 | 79.2 |  | C 67.09 | 66.90 |
|   |   |   |  | H 7.14 | 7.08 |
|   |   | 59.1 |  | N 5.81 | 5.82 |
| 5 | 5 | 69.8 |  | C 72.45 | 72.33 |
|   |   |   |  | H 8.16 | 8.09 |
|   |   | 52.2 |  | N 7.00 | 7.03 |
| 6 | 6 | 61.9 |  | C 67.43 | 67.48 |
|   |   |   |  | H 7.50 | 7.48 |
|   |   | 58.1 |  | N 6.29 | 6.30 |
| 7 | 7 | 49.5 |  | C 68.21 | 68.09 |
|   |   |   |  | H 7.65 | 7.54 |
|   |   | 40.5 (43.7) |  | N 5.50 | 5.45 |
| 8 | 8 | 73.2 |  | C 66.92 | 66.89 |
|   |   |   |  | H 7.32 | 7.25 |
|   |   | 63.3 |  | N 6.54 | 6.50 |
| 9 | 9 | 64.3 |  | C 73.24 | 73.14 |
|   |   |   |  | H 8.44 | 8.35 |
|   |   | 53.9 |  | N 6.78 | 6.82 |
| 10 | 10 | 59.3 |  | C 68.04 | 68.03 |
|   |   |   |  | H 7.70 | 7.69 |
|   |   | 50.1 |  | N 6.08 | 6.10 |
| 11 | 11 | 48.1 |  | C 68.11 | 68.03 |
|   |   |   |  | H 7.77 | 7.69 |
|   |   | 32.1 (39.7) |  | N 6.09 | 6.10 |
| 12 | 12 | 74.6 |  | C 67.39 | 67.48 |
|   |   |   |  | H 7.53 | 7.48 |
|   |   | 65.9 |  | N 6.32 | 6.30 |
| 13 | 17 | 56.6 |  | C 73.62 | 73.60 |
|   |   |   |  | H 8.71 | 8.69 |
|   |   | 32.1 (48.2) |  | N 6.36 | 6.36 |
| 14 | 18 | 53.6 |  | C 68.85 | 68.76 |
|   |   |   |  | H 8.00 | 8.04 |
|   |   | 43.7 (46.2) |  | N 5.65 | 5.73 |
| 15 | 19 | 47.8 |  | C 68.63 | 68.76 |
|   |   |   |  | H 8.21 | 8.04 |
|   |   | 9.0 (42.5) |  | N 5.73 | 5.73 |
| 16 | 20 | 59.5 |  | C 68.31 | 68.27 |
|   |   |   |  | H 7.88 | 7.85 |
|   |   | 37.0 (58.4) |  | N 5.95 | 5.90 |

In the above Table 4, a value within a parenthesis ( ) designates a monotropic temperature. Further, reference numerals C, N and I respectively designate a solid state of a crystalline, a nematic phase and an isotropic liquid.

Examples applied the optically active compound to the liquid crystal composition of the present invention will next be described.

EXAMPLE 17

A surface of each of two transparent electrodes is coated with polyvinyl alcohol (PVA) and is then rubbed to perform processing of parallel alignment. The two transparent electrodes are opposed and spaced 2 $\mu$m apart from each other in a state in which a PVA film is located on an inner side. Thus, a cell is formed between the two transparent electrodes. A composition is then implanted into this cell to produce a liquid crystal element. This composition is formed by mixing the optically active azo compound (compound No. 9) in the Example 9 with a liquid crystal composition ZLI-3234B indicative of a smectic C-phase manufactured by MERCK corp. at a mixture ratio of 10%.

EXAMPLES 18 TO 20

A composition is implanted into a cell similar to that in the example 17 to produce a liquid crystal element. This composition is made by mixing each of the optically active azo compounds (compound Nos. 10 to 12) in the Example 10 to 12 with the liquid crystal composition ZLI-3234B indicative of the smectic C-phase manufactured by MERCK corp. at a mixture ratio of 10%.

The following Table 5 shows values of phase transition temperatures of the above liquid crystal elements and values of spontaneous polarization thereof at the temperature of 250° C.

TABLE 5

| Example No. | compound No. | phase transition temperature (°C.) | | | | | spontaneous polarization (nC/cm$^2$) |
|---|---|---|---|---|---|---|---|
| | | C | SmC* | SmA | Ch | I | |
| 1 | 9 | | 71.0 | 75.6 | 93.5 | | 0.9 |
| | | | 70.2 | 74.9 | 93.1 | | |
| 2 | 10 | | 69.7 | 79.1 | 93.4 | | 20.5 |
| | | | 69.2 | 78.2 | 93.0 | | |
| 3 | 11 | | 71.0 | 80.9 | 92.5 | | 11.0 |
| | | −7.3 | 69.7 | 80.4 | 92.5 | | |
| 4 | 12 | | 70.4 | 78.8 | 94.1 | | 15.4 |
| | | −22.7 | 69.0 | 78.0 | 93.2 | | |

In the above Table 5, reference numerals C, SmC* and SmA respectively designate a solid state of a crystalline, a ferroelectric smectic C-phase and a smectic A-phase. Further, reference numerals Ch and I respectively designate a cholesteric phase and an isotropic liquid.

EXAMPLE 21

The optical active azo compounds (compound Nos. 9 and 10) are added at 10 weight % to a host liquid crystal ZLI-3234B having a smectic C-phase and manufactured by MERCK Corp. This added host liquid crystal is then inserted and sealed in a liquid crystal cell made by using a polyamide orientational agent. Faces of the liquid crystal are stuck to each other in a state in which rubbing directions of the liquid crystal are parallel to each other. A cell gap is controlled and set to 2.0 μm by sprinkling plastic beads in the liquid crystal. The following Table 6 shows an angle A formed between a rubbing direction and a extinction position of such a produced liquid crystal cell under crossed nicol. Table 6 also shows a dichroic ratio, and a cone angle and a response time when a voltage of ±15 V is applied to the liquid crystal cell.

TABLE 6

| compound No. | A/degree | dichroic ratio | cone angle/ degree | response time | spontaneous polarization/nCcm$^2$ |
|---|---|---|---|---|---|
| 9 | 16 | not less than 20 | 46 | 1.4 ms | 0.9 |
| 10 | 17 | not less than 20 | 57 | 0.25 ms | 20.5 |
| comparing example | 9 | 23 | 52 | 0.60 ms | 20.8 |

In a liquid crystal used in a comparing example in this Table 6, a dichroic dye G241 manufactured by Nihon photosensitive dye Co., Ltd. is added at 3.5 weight % to a ferroelectric liquid crystal CS-1018 manufactured by CHISSO Corp..

A memory capacity is considered to be increased as the angle A is increased. However, the angle A is equal to 8 to 12 degrees at most when the general dichroic dye is added to the ferroelectric liquid crystal as in the general case. Therefore, a case using the compound in the present invention is more excellent than the general case.

There is no large difference in each of the dichroic ratio and the cone angle between the present invention and the general case. However, the response time is much shorter than that in the general liquid crystal having the same spontaneous polarization. Accordingly, a liquid crystal composition using the compound in the present invention is clearly much more excellent than that in the general case.

As mentioned above, an optically active azo compound represented by the general formula (I) in the present invention has an excellent property and a high response speed and is chemically stable as a ferroelectric liquid crystal material, especially, in a composition constructed by mixing several kinds of compounds with each other. Further, this optically active azo compound has a very high response speed in comparison with the general compound in a guest-host mode in addition to a birefringent mode.

It is effective to prevent the generation of a reverse domain in a TN-type cell by adding the optically active azo compound represented by the general formula (I) to a nematic liquid crystal.

Accordingly, the optically active azo compound represented by the general formula (I) in the present invention can be used for a display and can be further used suitably for various kinds of electronic optical devices in a field of optoelectronics such as an electronic optical shutter, an electronic optical diaphragm, an optical modulator, a switch for switching optical communication paths, a memory, a varifocal lens, etc.

Many widely different example of the present invention may be constructed without departing from the spirit and scope of the present invention. It should be understood that the Present invention is not limited to the specific example described in the specification, except as defined in the appended claims.

What is claimed is:

1. An optically active azo compound represented by the following general formula (I),

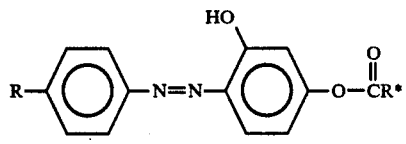

where R is an alkyl group having from 1 to 20 carbon atoms, and R* is a butyl group which is substituted by one of the halogen atoms selected from the group consisting of fluorine, chlorine and bromine.

2. An optically active azo compound represented by the following general formula (I),

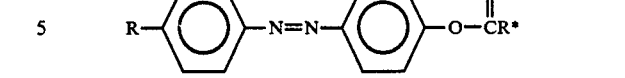

wherein R is an alkyl group having from 1 to 20 carbon atoms, and R* is a pentyl group which is substituted by one of the halogen atoms selected from the group consisting of fluorine, chlorine and bromine.

3. A liquid crystal composition containing an optically active azo compound represented by the following general formula (I),

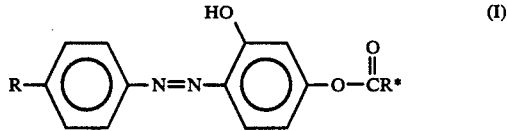

where R is an alkyl group having from 1 to 20 carbon atoms, and R* is an optically active radical of an alkyl group having from 1 to 10 carbons or a halogen substituted alkyl group having from 1 to 10 carbons, wherein the liquid crystal composition is mixed with a smectic liquid crystal which is not chiral in itself.

* * * * *